(12) United States Patent
Morishige et al.

(10) Patent No.: US 9,133,444 B2
(45) Date of Patent: Sep. 15, 2015

(54) METHOD FOR PRODUCING HYDROXYCARBOXYLIC ACID BY ENHANCING SYNTHESIS OF COENZYME

(75) Inventors: Takashi Morishige, Mobara (JP); Mitsufumi Wada, Mobara (JP); Hitoshi Takahashi, Chiba (JP); Daisuke Mochizuki, Mobara (JP); Junko Tokuda, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 282 days.

(21) Appl. No.: 13/618,898

(22) Filed: Sep. 14, 2012

(65) Prior Publication Data

US 2013/0029392 A1    Jan. 31, 2013

Related U.S. Application Data

(62) Division of application No. 12/299,646, filed as application No. PCT/JP2007/000470 on Apr. 27, 2007, now abandoned.

(30) Foreign Application Priority Data

May 9, 2006 (JP) ................. 2006-129984

(51) Int. Cl.
    C12P 7/42      (2006.01)
    C12N 1/20      (2006.01)
    C07H 21/02     (2006.01)
    C07H 21/04     (2006.01)
    C12N 9/10      (2006.01)

(52) U.S. Cl.
    CPC ............... *C12N 9/1077* (2013.01); *C12P 7/42* (2013.01); *C12Y 204/02011* (2013.01)

(58) Field of Classification Search
    CPC .................... C12N 9/1077; C12Y 204/02011; C12P 7/42
    See application file for complete search history.

(56) References Cited

U.S. PATENT DOCUMENTS

| 3,843,781 | A | 10/1974 | Masuda et al. |
| 5,602,941 | A | 2/1997 | Charles et al. |
| 6,087,140 | A | 7/2000 | Cameron et al. |
| 6,156,941 | A | 12/2000 | Ikai et al. |
| 2003/0032153 | A1 | 2/2003 | Yamamoto et al. |
| 2008/0032370 | A1* | 2/2008 | Wada et al. .................. 435/146 |

FOREIGN PATENT DOCUMENTS

| EP | 1 170 376 | | 1/2002 |
| EP | 1 748 076 | A1 | 1/2007 |
| JP | 10-174593 | A | 6/1998 |
| JP | 10-174594 | A | 6/1998 |
| JP | 2002-345479 | A | 12/2002 |
| JP | 2004-159587 | A | 6/2004 |
| JP | 2005-218349 | A | 8/2005 |
| JP | 2008-514338 | | 11/2007 |
| WO | WO 2005/106005 | A1 | 11/2005 |

OTHER PUBLICATIONS

Form PCT/ISA/210 (International Search Report) dated Jul. 17, 2007.
Laura Baldoma et al., *Involvement of Lactaldehyde Dehydrogenase in Several Metabolic Pathways of Escherichia Coli K12*, 262(29) The Journal of Biological Chemistry 13991-13996 (Oct. 15, 1987).
Susana J. Berrios-Rivera et al., *The Effect of Naprtase Overexpression on the Total Levels of NAD, the NADH/NAD+ Ratio, and the Distribution of Metabolites in Escherichia Coli*, 4 Metabolic Engineering 238-247 (2002).
John W. Foster et al., *Regulation of NAD metabolism in Salmonella typhimurium: Genetic analysis and cloning of the nadR repressor locus*, 208 Mol Gen Genet 279-287 (1987).
Anna V. Gerasimova et al., *Evolution of the NADR Regulon in Enterobacteriaceae*, 3(4) Bioinformatics and Computational Biology 1007-1019 (Aug. 2005).
R. K. Gholson et al., *Mode of Nicotinamide Adenine Dinucleotide Utilization by Escherichia coli*, 99(3) Journal of Bacteriology 895-896 (Sep. 1969).
Julianne H. Grose et al., *Regulation of NAD Synthesis by the Trifunctional NADR Protein of Salmonella Enterica*, 187(8) Journal of Bacteriology 2774-2782 (Apr. 2005).
Andrew Hacking et al., *Disruption of the Fucose Pathway as a Consequence of Genetic Adaptation to Propanediol as a Carbon Source in Escherichia coli*, 126(3) Journal of Bacteriology 1166-1172 (Jun. 1976).
Japanese Office Action in related application mailed Jun. 21, 2011, that cites JP 2008-514388.
Michihiko Kataoka et al., *Glycolic Acid Production Using Ethylene Glycol-Oxidizing Microorganisms*, 65(10) Biosci. Biotechnol. Biochem. 2265-2270 (2001).
Christopher L. Kitts et al., *Elucidation of the Complete Azorhizobium Nicotinate Catabolism Pathway*, 174(23) Journal of Bacteriology 7791-7797 (Dec. 1992).
Zhe Lu et al., *Evolution of an Escherichia coli Protein With Increased Resistance to Oxidative Stress*, 273(14) The Journal of Biological Chemistry 8308-8316 (Apr. 3, 1998).
Kenan C. Murphy et al., *PCR-mediated gene replacement in Escherichia coli*, 246 Gene 321-330 (2000).
L. N. Ornston et al., *Regulation of Glyoxylate Metabolism in Escherichia coli K-12*, 98(3) Journal of Bacteriology 1098-1108 (Jun. 1969).

(Continued)

*Primary Examiner* — Iqbal H Chowdhury
(74) *Attorney, Agent, or Firm* — Buchanan, Ingersoll & Rooney PC

(57) ABSTRACT

Hydroxycarboxylic acids are produced by using a microorganism that is improved in ability to produce nicotinamide adenine dinucleotide by deleting, mutating or substituting nadR gene in the microorganism or introducing a gene encoding nicotinic acid phosphoribosyltransferase.

3 Claims, 2 Drawing Sheets

(56) References Cited

OTHER PUBLICATIONS

Maria T. Pellicer et al., *Cross-induction of glc and ace Operons of Escherichia coli Attributable to Pathway Intersection*, 274(3) the Journal of Biological Chemistry 1745-1752 (1999).

L. Peng et al, *Global metabolic regulation analysis for Escherichia coli K12 based on protein expression by 2-dimensional electrophoresis and enzyme activity measurement*, 61 Appl. Microbiol. Biotechnol. 163-178 (2003).

Nadia Raffaelli et al., *The Escherichia Coli NADR Regulator Is Endowed With Nicotinamide Mononucleotide Adenylyltransferase Activity*, 181(17) Journal of Bacteriology 5509-5511 (Sep. 1999).

Supplementary European Search Report issued Nov. 8, 2011, in related European Patent Application No. 07737126.8-1521 / 2025759.

Gerald Tritz and Jerry Lr Chandler, *Recognition of a Gene Involved in the Regulation of Nicotinamide Adenine Dinucleotide Biosynthesis*, 114(1) Journal of Bacteriology 128-136 (Apr. 1973).

Marcel G. Wubbolts et al., *Variation of Cofactor Levels in Escherichia Coli*, 265(29) The Journal of Biological Chemistry 17665-17672 (Oct. 15, 1990).

Ning Zhu et al., *Activity of the Nicotinamide Mononucleotide Transport System Is Regulated in Salmonella typhimurium*, 173(3) Journal of Bacteriology 1311-1320 (Feb. 1991).

\* cited by examiner

SEQUENCE LISTING

<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: Primer for PCR

<400> SEQUENCE: 1
aggaagtgcc attctgattg g

```
<210> SEQ ID NO 2
<211> LENGTH: 30
<212> TYPE: DNA
<213> ORGANISM: Artificial Sequence
<220> FEATURE:
<223> OTHER INFORMATION: Primer for PCR

<400> SEQUENCE: 2
ggaattcgta tatctcatta taagtcgtcg                                            30

<210> SEQ ID NO 3
<211> LENGTH: 27
<212> TYPE: DNA
<213> ORGANISM: Artificial Sequence
<220> FEATURE:
<223> OTHER INFORMATION: Primer for PCR

<400> SEQUENCE: 3
ggaattcgtg atgaaactgc tcaaagg                                               27

<210> SEQ ID NO 4
<211> LENGTH: 27
<212> TYPE: DNA
<213> ORGANISM: Artificial Sequence
<220> FEATURE:
<223> OTHER INFORMATION: Primer for PCR

<400> SEQUENCE: 4
ttggtacctg atgacctgag cttctcg                                               27

<210> SEQ ID NO 5
<211> LENGTH: 27
<212> TYPE: DNA
<213> ORGANISM: Artificial Sequence
<220> FEATURE:
<223> OTHER INFORMATION: Primer for PCR

<400> SEQUENCE: 5
ttggtaccgt tctgccagca actgacg                                               27

<210> SEQ ID NO 6
<211> LENGTH: 28
<212> TYPE: DNA
<213> ORGANISM: Artificial Sequence
<220> FEATURE:
<223> OTHER INFORMATION: Primer for PCR

<400> SEQUENCE: 6
tgtctagagt acctctgtgc gtcactgg                                              28

<210> SEQ ID NO 7
<211> LENGTH: 28
<212> TYPE: DNA
<213> ORGANISM: Artificial Sequence
<220> FEATURE:
<223> OTHER INFORMATION: Primer for PCR

<400> SEQUENCE: 7
gctctagacg ctttgttgtg ttgtgtgg                                              28

<210> SEQ ID NO 8
<211> LENGTH: 28
<212> TYPE: DNA
<213> ORGANISM: Artificial Sequence
<220> FEATURE:
```

<223> OTHER INFORMATION: Primer for PCR

<400> SEQUENCE: 8
aactgcagga tcggtcaatg attgcagc                                28

<210> SEQ ID NO 9
<211> LENGTH: 26
<212> TYPE: DNA
<213> ORGANISM: Artificial Sequence
<220> FEATURE:
<223> OTHER INFORMATION: Primer for PCR

<400> SEQUENCE: 9
cagctgactc gacatcttgg ttaccg                                  26

<210> SEQ ID NO 10
<211> LENGTH: 27
<212> TYPE: DNA
<213> ORGANISM: Artificial Sequence
<220> FEATURE:
<223> OTHER INFORMATION: Primer for PCR

<400> SEQUENCE: 10
cagctgcaag agggtcatta tatttcg                                 27

<210> SEQ ID NO 11
<211> LENGTH: 45
<212> TYPE: DNA
<213> ORGANISM: Artificial Sequence
<220> FEATURE:
<223> OTHER INFORMATION: Primer for PCR

<400> SEQUENCE: 11
gctctagacg gagaaagtct tatgatggct aacagaatga ttctg             45

<210> SEQ ID NO 12
<211> LENGTH: 29
<212> TYPE: DNA
<213> ORGANISM: Artificial Sequence
<220> FEATURE:
<223> OTHER INFORMATION: Primer for PCR

<400> SEQUENCE: 12
gtgaagcttg catttaccag gcggtatgg                               29

<210> SEQ ID NO 13
<211> LENGTH: 43
<212> TYPE: DNA
<213> ORGANISM: Artificial Sequence
<220> FEATURE:
<223> OTHER INFORMATION: Primer for PCR

<400> SEQUENCE: 13
cgaattccgg agaaagtctt atgtcagtac ccgttcaaca tcc               43

<210> SEQ ID NO 14
<211> LENGTH: 29
<212> TYPE: DNA
<213> ORGANISM: Artificial Sequence
<220> FEATURE:
<223> OTHER INFORMATION: Primer for PCR

<400> SEQUENCE: 14
gctctagact ctttcactca ttaagactg                               29

```
<210> SEQ ID NO 15
<211> LENGTH: 30
<212> TYPE: DNA
<213> ORGANISM: Artificial Sequence
<220> FEATURE:
<223> OTHER INFORMATION: Primer for PCR

<400> SEQUENCE: 15
aacgaattct cgcaatgatt gacacgattc                                         30

<210> SEQ ID NO 16
<211> LENGTH: 32
<212> TYPE: DNA
<213> ORGANISM: Artificial Sequence
<220> FEATURE:
<223> OTHER INFORMATION: Primer for PCR

<400> SEQUENCE: 16
acagaattcg ctatttgtta gtgaataaaa gg                                      32

<210> SEQ ID NO 17
<211> LENGTH: 47
<212> TYPE: DNA
<213> ORGANISM: Artificial Sequence
<220> FEATURE:
<223> OTHER INFORMATION: Primer for PCR

<400> SEQUENCE: 17
cgaattccgg agaaagtctt atgactacgg cattgaaaaa gattgtg                      47

<210> SEQ ID NO 18
<211> LENGTH: 29
<212> TYPE: DNA
<213> ORGANISM: Artificial Sequence
<220> FEATURE:
<223> OTHER INFORMATION: Primer for PCR

<400> SEQUENCE: 18
ggtctagacg attaatgcaa cttcaaacg                                          29

<210> SEQ ID NO 19
<211> LENGTH: 43
<212> TYPE: DNA
<213> ORGANISM: Artificial Sequence
<220> FEATURE:
<223> OTHER INFORMATION: Primer for PCR

<400> SEQUENCE: 19
cgtgcaattg ccggagaaag tcttatgaca caattcgctt ctc                          43

<210> SEQ ID NO 20
<211> LENGTH: 32
<212> TYPE: DNA
<213> ORGANISM: Artificial Sequence
<220> FEATURE:
<223> OTHER INFORMATION: Primer for PCR

<400> SEQUENCE: 20
cgctctagat taactggctt ttttaatatg cg                                      32

<210> SEQ ID NO 21
<211> LENGTH: 32
<212> TYPE: DNA
<213> ORGANISM: Artificial Sequence
<220> FEATURE:
<223> OTHER INFORMATION: Primer for PCR
```

```
<400> SEQUENCE: 21
aaaataagct tcgattaatg caacttcaaa cg                                    32
```

METHOD FOR PRODUCING HYDROXYCARBOXYLIC ACID BY ENHANCING SYNTHESIS OF COENZYME

This application is a Divisional Application of U.S. patent application Ser. No. 12/299,646, filed on Nov. 5, 2008, now abandoned, which is a U.S. National Stage of PCT/JP2007/000470, filed on Apr. 27, 2007, which designated the United States and was published in the English language on Nov. 15, 2007, as WO 2007/129465 A1 and claims priority under 35 U.S.C. §119 to JP 2006-129984, filed on May 9, 2006; and the content of each is hereby expressly incorporated by reference in their entireties for all purposes and each is assigned to the assignee hereof.

TECHNICAL FIELD

The present invention relates to a microorganism which produces hydroxycarboxylic acids including glycolic acid and a method for producing hydroxycarboxylic acids including glycolic acid by using the microorganism.

BACKGROUND ART

Since hydroxycarboxylic acids are useful as a raw material for polymers or an intermediate for medicines, a method for effectively producing hydroxycarboxylic acids have been demanded.

As an example, glycolic acid (α-hydroxyacetic acid) can be mentioned. Glycolic acid has been used as a raw material for cleaning agents or cosmetics, but has recently received attention as a raw material for polyglycolic acid which is useful as a gas barrier polymer or a medical polymer. The reason why glycolic acid has received attention as a gas barrier material is that a layer of polyglycolic acid has high oxygen barrier property and performance as a material for packing food or carbonated beverage which can easily spoil in the presence of oxygen.

Glycolic acid of a chemically synthesized product which is currently commercially available contains quite a few impurities, which is a problem when used as a raw material for polymers in view of purity. This is because these impurities inhibit a dehydrating condensation reaction of glycolic acid, and also methoxy acetate which is one of those impurities is a compound suspicious of carcinogenic potential, thus being desirable not to be included in a packing material for food or beverage. Of course, it is technically possible to remove impurities by purification, but such the purified products are actually high in cost and thus are not practical as a raw material for packing at low cost.

In order to avoid the aforementioned problems given in glycolic acid of chemically synthesized products, a production of glycolic acid according to a biomethod employing ethylene glycol as a raw material has been attempted.

In Patent Document 1 and Patent Document 2, there has been disclosed a method for producing glycolic acid by a microorganism, which includes culturing yeast belonging to genus *Pichia*, genus *Rhodotorula*, genus *Sporobolomyces*, genus *Kluyveromyces* or genus *Torulopsis*, a strain belonging to genus *Nocardia*, a strain belonging to genus *Rhodococcus*, or an *Escherichia coli* B strain in a culturing medium containing ethylene glycol and separating and collecting glycolic acid from the culturing broth.

Among the methods for producing glycolic acid as described in Examples of Patent Document 1 and Patent Document 2, a method employing *Pichia naganishii* gives the highest accumulation concentration of glycolic acid, and 35.3 g/L of glycolic acid is obtained by a reaction for 30 hours. In regard to the production of glycolic acid with the use of *Pichia naganishii*, it has been reported in Non-Patent Document 1 that 105 g/L of glycolic acid can be obtained by a reaction for 120 hours with further improved reaction conditions.

In Patent Document 3, it has been described that it is possible to produce hydroxycarboxylic acids including glycolic acid from a raw material like aliphatic polyhydric alcohols having a hydroxyl group at the end such as ethylene glycol, by using a microorganism in which a gene encoding lactaldehyde reductase and a gene encoding lactaldehyde dehydrogenase are introduced in the form of plasmid so as to impart or enhance an activity of those enzymes, as well as described that an ability to produce glycolic acid is improved by disrupting a gene encoding glycolate oxidase contained in a microorganism so as to inactivate an activity of the enzyme.

In a reaction for producing hydroxycarboxylic acids including glycolic acid by the above-mentioned conventional methods, an amount of microbial cell required for the reaction is large, which thereby causes problems such as an increase in the production cost, contamination by impurities derived from the microbial cells, and requiring so much work and cost for disposing the microbial cells after the production of hydroxycarboxylic acids.

As a biosynthesis pathway of nicotinamide adenine dinucleotide in a microorganism, there are a pathway (de novo pathway) in which a biological synthesis is done via quinolic acid from aspartic acid and a pathway (recycle pathway) in which nicotinamide produced by a metabolization of nicotinamide adenine dinucleotide and so on is recycled. It has been known that the biosynthesis pathways thereof in an Enterobacteriaceae family including genus *Escherichia*, genus *Shigella*, genus *Salmonella*, genus *Erwinia*, genus *Yersinia* and genus *Photorhabdus* is controlled by a protein (hereinafter, referred to as NadR) encoded by nadR (may be referred to as nadI according to literatures) gene. In specific, it has been known that NadR inhibits the expressions of an L-aspartic acid oxidase gene and a quinolinic acid synthetase gene in the de novo pathway, as well as a nicotinic acid phosphoribosyltransferase gene (hereinafter, referred to as pncB) in the recycle pathway.

On the other hand, NadR as a multifunctional protein has important functions as described below in the biosynthesis of nicotinamide adenine dinucleotide as described below. That is, it is clear that NadR also has functions as a transfer of nicotinamide mononucleotide which is a precursor for nicotinamide adenine dinucleotide, as well as a function as nicotinamide mononucleotide adenylyltransferase catalyzing the reaction for producing deamide-nicotinamide adenine dinucleotide which is a precursor for nicotinamide adenine dinucleotide from ATP and nicotinic acid ribonucleotide.

Microorganisms in which nadR gene is disrupted have been already reported in Non-Patent Document 2, but a production of hydroxycarboxylic acids by such the microorganisms has not bee reported.

In Non-Patent Document 3, it has been reported that the content of nicotinamide adenine dinucleotide is enhanced by introducing a pncB expression vector to *Escherichia coli*.

[Patent Document 1] Japanese Patent Laid-open No. H10-174593

[Patent Document 2] Japanese Patent Laid-open No. H10-174594

[Patent Document 3] International Publication Pamphlet No. WO 2005/106005

[Non-Patent Document 1] Biosci. Biotechnol. Biochem., Vol. 65 (10), pp. 2265-2270, (2001)

[Non-Patent Document 2] J. Bacteriol., Vol. 187 (8), pp. 2774-2784, (2005)

[Non-Patent Document 3] Metabolic Engineering, Vol. 4, pp. 238-247, (2002)

DISCLOSURE OF THE INVENTION

It is an object of the present invention to provide a method for producing hydroxycarboxylic acids by microorganism, by which hydroxycarboxylic acids can be efficiently produced using a small amount of microbial cell, and a microorganism suitable for the production method.

From the results of studies to solve the above objects, the present inventors have found that hydroxycarboxylic acids can be efficiently produced by using a microorganism in which an ability to produce nicotinamide adenine dinucleotide is enhanced, in a method for producing a hydroxycarboxylic acid from aliphatic polyhydric alcohol having a hydroxyl group at the end by using a microorganism.

That is, the present invention is as described by [1] to [19] herein below.

[1] A method for producing a hydroxycarboxylic acid from an aliphatic polyhydric alcohol having a hydroxyl group at the end by using a microorganism, where the method includes using the microorganism which has an enhanced ability to produce nicotinamide adenine dinucleotide.

[2] The production method of [1], wherein the microorganism is provided with enhanced ability to produce nicotinamide adenine dinucleotide by performing at least one genetic manipulation of the following (1) and (2):
(1) deleting, mutating or substituting nadR gene in the microorganism; and
(2) introducing into the microorganism a plasmid integrated with a gene of nicotinic acid phosphoribosyltransferase in the microorganism.

[3] The production method as set forth in [1], wherein the microorganism has an enhanced ability to regenerate oxidized form of nicotinamide adenine dinucleotide.

[4] The production method of [3], wherein the microorganism is provided with enhanced ability to regenerate oxidized form of nicotinamide adenine dinucleotide by introducing a plasmid integrated with a gene of NADH dehydrogenase.

[5] The production method as set forth in [1], wherein the microorganism has enhanced activity of at least one enzyme of lactaldehyde reductase and lactaldehyde dehydrogenase.

[6] The production method as set forth in [3], wherein the microorganism has enhanced activity of at least one enzyme of lactaldehyde reductase and lactaldehyde dehydrogenase.

[7] The production method as set forth in any one of [1], [3], [5] and [6], wherein the microorganism has inactivated or lowered activity of glycolate oxidase as compared to the activity of existing microorganism.

[8] The production method as set forth in any one of [1] to [7], wherein the aliphatic polyhydric alcohol having a hydroxyl group at the end is ethylene glycol and the hydroxycarboxylic acid is glycolic acid.

[9] A microorganism, wherein an activity of at least one enzyme of lactaldehyde reductase and lactaldehyde dehydrogenase is enhanced, and an ability to produce nicotinamide adenine dinucleotide is enhanced by performing at least one gene manipulation of the following (1) and (2):
(1) deleting, mutating or substituting nadR gene in the microorganism; and
(2) introducing into the microorganism a plasmid integrated with a gene of nicotinic acid phosphoribosyltransferase in the microorganism.

[10] The microorganism as set forth in [9], wherein an ability to regenerate oxidized form of nicotinamide adenine dinucleotide is enhanced.

[11] A microorganism, wherein an activity of NADH dehydrogenase is enhanced, and an ability to produce nicotinamide adenine dinucleotide is enhanced by performing at least one gene manipulation of the following (1) and (2):
(1) deleting, mutating or substituting nadR gene in the microorganism; and
(2) introducing into the microorganism a plasmid integrated with a gene of nicotinic acid phosphoribosyltransferase in the microorganism.

[12] The microorganism as set forth in [9] or [10], wherein the activity of glycolate oxidase is inactivated or lowered than the activity of the existing microorganism.

[13] The microorganism as set forth in [11], wherein the activity of glycolate oxidase is inactivated, or lowered than the activity of the existing microorganism.

[14] The production method as set forth in any one of [1] to [8], wherein the microorganism is any one of genus *Escherichia*, genus *Shigella*, genus *Salmonella*, genus *Erwinia*, genus *Yersinia* and genus *Photorhabdus*.

[15] The production method as set forth in [14], wherein the microorganism is *Escherichia coli*.

[16] The microorganism as set forth in any one of [9], [10] and [12], which is any one of genus *Escherichia*, genus *Shigella*, genus *Salmonella*, genus *Erwinia*, genus *Yersinia* and genus *Photorhabdus*.

[17] The microorganism as set forth in [11]) or [13], which is any one of genus *Escherichia*, genus *Shigella*, genus *Salmonella*, genus *Erwinia*, genus *Yersinia* and genus *Photorhabdus*.

[18] The microorganism as set forth in [16], which is *Escherichia coli*.

[19] The microorganism as set forth in [17], which is *Escherichia coli*.

According to the present invention, hydroxycarboxylic acids can be efficiently produced using a small amount of microbial cell. Further, according to the present invention, a microorganism suitable for producing hydroxycarboxylic acids can be provided.

BRIEF DESCRIPTION OF THE DRAWINGS

The above objects and other objects, features and advantages will be clearer with reference to the best modes for carrying out the invention and the figures described hereinafter.

Figure 1:
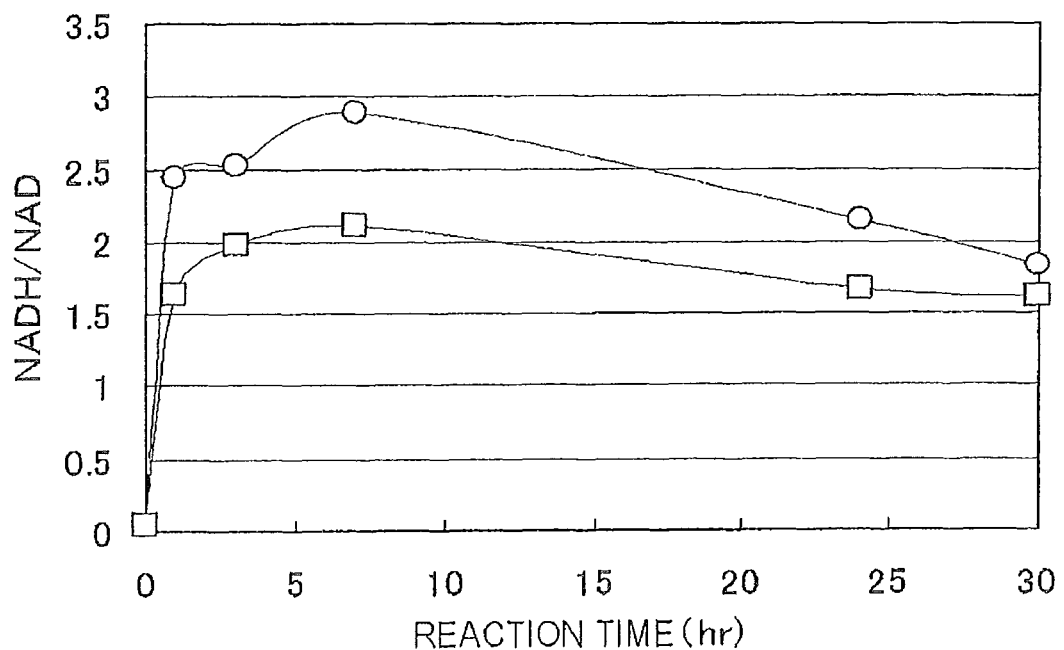
FIG. 1 It is a graph which shows the time-course change in the NADH/NAD ratio (the NADH content/the NAD content) in the cell in Reference Example 3:
□ in the figure indicates the NADH/NAD ratio of ΔnadRΔglcDEF/pGAPfucO-aldA-ndh strain;
○ in the figure indicates the NADH/NAD ratio of ΔnadRΔglcDEF/pGAPfucO-aldA strain.

○ in the figure indicates the results from the reaction at pH 7.7;

Δ in the figure indicates the results from the reaction at pH 7.2;

□ in the figure indicates the results from the reaction at pH 6.5;

x in the figure indicates the results from the reaction at pH 6.0;

◇ in the figure indicates the results from the reaction at pH 4.3.

BEST MODE FOR CARRYING OUT THE INVENTION

The present embodiment will be described in more detail below.

The present invention relates to a method for producing a hydroxycarboxylic acid. This method is a method for producing a hydroxycarboxylic acid from an aliphatic polyhydric alcohol having a hydroxyl group at the end by using a microorganism, which comprises using the microorganism in which an ability to produce nicotinamide adenine dinucleotide is enhanced.

The microorganism may be any of those capable of having an ability to produce a hydroxycarboxylic acid from an aliphatic polyhydric alcohol having a hydroxyl group at the end by using any means, regardless of whether or not it inherently has an ability to produce a hydroxycarboxylic acid from an aliphatic polyhydric alcohol having a hydroxyl group at the end. As such a microorganism, there may be exemplified by preferably microorganisms belonging to genus *Escherichia*, genus *Shigella*, genus *Salmonella*, genus *Erwinia*, genus *Yersinia* and genus *Photorhabdus*, and more preferably *Escherichia coli*.

Further, the aliphatic polyhydric alcohol is not particularly limited in its structure if it is an aliphatic compound having a hydroxyl group having at the end of a carbon chain and having at least two hydroxyl groups in the molecule, but examples of such a compound may include ethylene glycol, diethylene glycol, glycerol, 1,3-propanediol, 1,2-butanediol, 1,3-butanediol, 1,4-butanediol, 1,2,4-butanetriol and the like.

Further, the hydroxycarboxylic acid refers to a compound in which one of the end carbons having hydroxyl groups in the molecule of the aliphatic polyhydric alcohol having a hydroxyl group at the end is oxidized to be a carboxylic acid. Examples of such a compound may include glycolic acid, hydroxyethoxyacetic acid, glyceric acid, 3-hydroxypropionic acid, 2-hydroxybutanoic acid, 3-hydroxy hydroxybutanoic acid, 4-hydroxy hydroxybutanoic acid, 2,4-dihydroxy hydroxybutanoic acid and the like.

In the present embodiment, ethylene glycol may be properly used as the aliphatic polyhydric alcohol having a hydroxyl group at the end. Further, glycolic acid may be properly used as the hydroxycarboxylic acid.

The microorganism related to the present embodiment is provided with enhanced ability to produce nicotinamide adenine dinucleotide by performing at least one gene modification of the following (1) and (2):

(1) deleting, mutating or substituting nadR gene in the microorganism; and (2) introducing a plasmid integrated with a gene of nicotinic acid phosphoribosyltransferase in the microorganism.

Here, the nicotinamide adenine dinucleotide refers to any of its oxidized form and its reduced type if not specified.

The term 'ability to produce nicotinamide adenine dinucleotide is enhanced' refers to a state where the total content of the oxidized-form nicotinamide adenine dinucleotide (may be abbreviated as NAD hereinafter) and the reduced-type nicotinamide adenine dinucleotide (may be abbreviated as NADH hereinafter) in a microorganism is significantly enhanced with respect to a wild strain of the microorganism (or the microorganism prior to recombination), in which the total content of NAD and NADH is preferably from 1.2 times to 10 times that of the microorganism prior to such enhancement.

Further, as for nadR gene, exemplifying an *Escherichia coli* MG1655 strain, the nadR gene is encoded in Based No. 4625317 to 4626570 in the entire base sequence of the genome DNA of the *Escherichia coli* MG1655 strain (GenBank accession number U00096). Also, the nadR gene of *Salmonella typhimurium* is evident by GenBank accession number M85181. It has been evident that the nadR gene exists in the Enterobacteriaceae family including genus *Shigella*, genus *Erwinia*, genus *Yersinia* and genus *Photorhabdus*, other than the above microorganisms (Gerasimova, A V., et. al., Journal of Bioinformatics and Computational Biology, Vol. 3, pp. 1007-1019 (2005)).

A microorganism subjected to deletion, mutation or substitution for the nadR gene can be obtained by common methods known to a person having an ordinary skill in the art. As an example of such a microorganism subjected to deletion, mutation or substitution for the nadR gene, an *Escherichia coli* MT-11032 strain may be mentioned.

In the method for producing a hydroxycarboxylic acid, *Escherichia coli* MT-11032 strain may be used. In the *Escherichia coli* MT-11032 strain, the nadR gene is substituted by a kanamycin resistant gene and activity of glycolate oxidase is inactivated by that glcDEF, a gene encoding glycolate oxidase as described below, is substituted by a tetracycline resistant gene. The present strain has been deposited as the deposition number FERM BP-10773 at International Patent Organism Depository Center of National Institute of Advanced Industrial Science and Technology at Tsukuba Central 6, 1-1-1 Higashi, Tsukuba, Ibaraki, Japan, based on the Budapest Treaty on the International Recognition of the Deposit of Microorganisms for the Purposes of Patent Procedure. Further, this deposition has been transferred from FERM P-20797 deposited on Feb. 14, 2006.

Here, the nicotinic acid phosphoribosyltransferase is classified into the enzyme number 2.4.2.11, based on the report of the enzyme committee of International Union of Biochemistry (I.U.B.), and refers to a generic name of an enzyme which reversibly catalyzes a reaction to produce nicotinic acid mononucleotide from nicotinic acid and 5-phosphoribosyl-1α-2 phosphoric acid.

Using a microorganism in which a plasmid integrated with a gene (may be referred to as pncB hereinafter) of nicotinic acid phosphoribosyltransferase is introduced, a hydroxycarboxylic acid can be produced from an aliphatic polyhydric alcohol having a hydroxyl group at the end. Preparation of the genome DNA used for introducing a gene into a microorganism, preparation of a plasmid, digestion and ligation of DNA, transformation, PCR (Polymerase Chain Reaction), design and synthesis of oligonucleotide used as a primer and the like can be carried out according to usual methods well known to the skilled person in the art. These methods have been disclosed in Sambrook, J., et al., "Molecular Cloning A Laboratory Manual, Second Edition", Cold Spring Harbor Laboratory Press, (1989) and the like.

Furthermore, the microorganism related to the present embodiment has enhanced ability to regenerate oxidized form of nicotinamide adenine dinucleotide. Here, the enhanced ability to regenerate NAD means a state in which an activity of an enzyme catalyzing a reaction of transforming NADH which is produced from the production of a hydroxycarboxylic acid by an oxidation reaction of aliphatic polyhydric alcohol having a hydroxyl group at the end into NAD is significantly enhanced compared with the activity before the enhancement. As such an enzyme, there may be mentioned glutamic acid dehydrogenase, glucose dehydrogenase, NADH oxidase, NADH dehydrogenase and the like. When the ability to regenerate NAD is enhanced, it is preferable that compounds which may be burdened in subsequent processes such as purification and the like be not increased. As the enzyme catalyzing a reaction of transforming NADH to NAD, NADH dehydrogenase is preferred. For example, when NADH dehydrogenase derived from *Escherichia coli* is the enzyme catalyzing a reaction of transforming NADH to NAD, it is preferable that the activity be enhanced by 2 times or more as compared with a wild strains (or a microorganism prior to recombination).

Such the microorganisms having enhanced enzyme activity can be produced, for example, by using a method of introducing a gene encoding the enzyme into a wild type microorganism (or a microorganism prior to recombination) using a gene recombination technique, a method of introducing a mutant to a promoter of a gene encoding the enzyme in the genome, and the like. As a method for introducing the gene into the wild type microorganism (or a microorganism prior to recombination), there may be mentioned by a method of introducing the gene into the microorganism in the form of plasmid. Preparation of the genome DNA used for introduction of a gene into a microorganism, preparation of plasmid, cleavage and ligation of DNA, transformation, PCR, design and synthesis of oligonucleotide to be used as a primer and the like can be carried out according to a usual methods well known to the skilled person in the art. These methods have been disclosed in the above-mentioned literature by Sambrook, J., et al.

Further, the microorganism related to the present embodiment is provided with an enhanced ability to regenerate oxidized-form nicotinamide adenine dinucleotide by introducing a plasmid integrated with a gene of NADH dehydrogenase. Here, the NADH dehydrogenase is classified into the enzyme number 1.6.5.3, 1.6.99.3 or 1.6.99.5, based on the report of the enzyme committee of International Union of Biochemistry (I.U.B.), and refers to a generic name of an enzyme which reversibly catalyzes a reaction to generate NAD from NADH using quinones such as ubiquinone, dimethylmenaquinone, menaquinone and the like as an electron acceptor. Preferred is the NADH dehydrogenase which is classified into the enzyme number 1.6.99.3, based on the report of the enzyme committee of International Union of Biochemistry (I.U.B.), and for example, in *Escherichia coli*, the NADH dehydrogenase encoded at the ndh gene which is reported by GenBank accession number V00306 may be exemplified.

In the present embodiment, a hydroxycarboxylic acid can be produced from aliphatic polyhydric alcohols having a hydroxyl group at the end by using a microorganism in which a plasmid integrated with a gene of NADH dehydrogenase is introduced. Construction of a necessary plasmid or introduction of a plasmid in a microorganism can be carried out according to a usual method well known to the skilled person in the art.

Further, a microorganism related to the present embodiment has enhanced activity of at least one enzyme of lactaldehyde reductase and lactaldehyde dehydrogenase. Here, the lactaldehyde reductase is classified into the enzyme number 1.1.1.77 based on the report of the enzyme committee of I.U.B., and refers to a generic name of an enzyme that reversibly catalyzes a reaction to produce lactaldehyde from 1,2-propanediol in the presence of NAD which is a coenzyme.

Further, the lactaldehyde dehydrogenase is classified into the enzyme number 1.2.1.22 based on the report of the enzyme committee of I.U.B. and refers to a generic name of an enzyme that catalyzes a reaction to produce lactic acid from lactaldehyde in the presence of NAD which is a coenzyme, and also the lactaldehyde dehydrogenase is classified into the enzyme number 1.2.1.21 based on the report of the enzyme committee of I.U.B. and refers to a generic name of an enzyme glycolaldehyde dehydrogenase that catalyzes a reaction to produce glycolic acid from glycolaldehyde in the presence of NAD which is a coenzyme. This is because there has been reported in the previous literature using *Escherichia coli* that lactaldehyde dehydrogenase and glycolaldehyde dehydrogenase are the same enzyme (Caballero, E., et al., J. Biol. Chem., Vol. 258 (12), pp. 7788-7792 (1983).

The term 'at least one enzyme of lactaldehyde reductase and lactaldehyde dehydrogenase is enhanced' means that, for example, in *Escherichia coli*, activity of at least one enzyme of these enzymes is preferably enhanced by 20 times or more, and more preferably by 100 times or more, in comparison with a wild strain (or a microorganism prior to recombination). These microorganisms which are enhanced in activity of the enzyme can be produced, for example, by using a method of introducing a gene encoding the enzyme into a wild type microorganism (or a microorganism before recombination) using a gene recombination technique, a method of introducing a mutation to a promoter of a gene encoding the enzyme in the genome, or the like. As a method for introducing the gene into the wild type microorganism (or a microorganism prior to recombination), a method for introducing the gene into the microorganism in the form of plasmid can be mentioned. Preparation of the genome DNA used for introduction of a gene into a microorganism, preparation of plasmid, cleavage and ligation of DNA, transformation, PCR (Polymerase Chain Reaction), design and synthesis of oligonucleotide used as a primer and the like can be carried out according to a usual method well known to the skilled person in the art. These methods have been disclosed in the above-mentioned literature by Sambrook, J., et al.

For example, *Escherichia coli* that is enhanced in the enzyme activity of lactaldehyde reductase and Lactaldehyde dehydrogenase can be prepared as described below.

The base sequence of the gene (hereinafter may be abbreviated as fucO) of lactaldehyde reductase of *Escherichia coli* has been already reported (GenBank accession number M31059). Further, the base sequence of the gene (hereinafter may be abbreviated as aldA) of lactaldehyde dehydrogenase of *Escherichia coli* has been also already reported (GenBank accession number M64541).

In order to acquire fucO, oligonucleotide to be a primer is used for a PCR amplification using the genome DNA of *Escherichia coli* as a template, and the obtained DNA fragment was digested with a restriction enzyme to obtain a fucO fragment.

Further, in order to acquire aldA, oligonucleotide to be a primer is used for a PCR amplification using the genome DNA of *Escherichia coli* as a template, and the obtained DNA fragment was digested with a restriction enzyme to obtain an aldA fragment.

Also, in order to acquire a glyceraldehyde 3-phosphate dehydrogenase (GAPDH) promoter, oligonucleotide to be a primer is used for a PCR amplification using the genome DNA of *Escherichia coli* as a template, and the obtained DNA fragment was digested with a restriction enzyme to obtain a DNA fragment encoding a GAPDH promoter.

The above 3 DNA fragments are ligated with a fragment obtained by digesting a plasmid with a restriction enzyme and then transformed with *Escherichia coli* to obtain a transformant which grows on an LB agar plate. The obtained colony was cultured in an LB liquid culture medium and the plasmid is recovered from the obtained microbial cells. By introducing the plasmid into any host *Escherichia coli*, *Escherichia coli* which is enhanced in enzyme activity of lactaldehyde reductase and lactaldehyde dehydrogenase can be prepared.

In the microorganisms related to the present embodiment, activity of glycolate oxidase is inactivated or decreased as compared to the activity of existing microorganisms.

Here, the glycolate oxidase is classified into the enzyme number 1.1.3.15, based on the report of the enzyme committee of I.U.B. and refers to a generic name of an enzyme that reversibly catalyzes a reaction to produce glyoxylic acid from glycolic acid.

The inactivation of glycolate oxidase activity means complete loss of activity of the enzyme. And the decrease of glycolate oxidase activity means that activity of the enzyme is partly lost, and preferably a half or less, more preferably one tenth or less, with respect to inherent glycolate oxidase activity of a wild strain (or a microorganism prior to recombination). In order to inactivate or decrease activity of glycolate oxidase, there are methods such as introducing a mutation to the gene (may be abbreviated as glcDEF gene hereinafter) encoding the protein, deleting the gene, or adding a medicine which specifically inactivates the protein, irradiating with ultraviolet rays or the like. Gene modification such as the introduction of a mutation or deletion to the gene can be carried out by a common method known to a person skilled in the art. Specifically, an *Escherichia coli* MT-11023 strain can be mentioned as a microorganism in which activity of glycolate oxidase is inactivated by substituting glcDEF gene with a tetracycline resistant gene.

In the present embodiment, the term "in the form of plasmid" when introducing a gene encoding a certain target enzyme into a microorganism refers to preparation of a recombinant plasmid by ligating the gene to a vector and introduction of the prepared plasmid into the microorganism by a method of transformation or the like.

Also, when a purposed gene is functionally ligated to a strong promoter constitutively functioning in a microorganism, it is possible to achieve the object of the present invention by using a plasmid in which the number of copies per microorganism cell is generally known to be low due to a property of replicon in a plasmid. As the plasmid having such a replicon, pACYC184 (GenBank accession number: X06403) and the like can be exemplified.

When carrying out the production method of the present embodiment, a necessary amount of microbial cells of microorganism is obtained usually by culturing and growing a microorganism using a culture medium.

The culture medium to be used for the culture according to the present embodiment is not particularly limited if it is a culture medium containing carbon source, nitrogen source, inorganic ion and optionally traces of other organic components. As the carbon source, saccharides such as glucose, fructose, molasses and the like; organic acids such as fumaric acid, citric acid, succinic acid and the like; and alcohols such as methanol, ethanol, glycerol and others are properly used. As nitrogen source, inorganic and organic nitrogen sources such as organic ammonium salts, inorganic ammonium salts, ammonia gas, ammonia water, protein hydrolysates and the like are properly used. As inorganic ion, magnesium ion, phosphate ion, potassium ion, iron ion, manganese ion, sulfate ion and others are properly used as required. As traces of organic components, vitamin, amino acid and the like and yeast extract containing vitamin, amino acid and the like, peptone, corn steep liquor, casein hydrolysate and others are properly used.

As the culture medium to be used for the culture, preferably used is a liquid culture medium considering that a microorganism is provided for the industrial production.

Further, a composition of the culture medium is preferable to be polypeptone of from 0.5 g/L to 10 g/L, $Fe_2SO_4$ of from 0.02 g/L to 0.3 g/L, $K_2HPO_4$ of from 0.5 g/L to 5 g/L, $KH_2PO_4$ of from 0.5 g/L to 5 g/L, $MgSO_4.7H_2O$ of from 0.5 g/L to 5 g/L, $(NH_4)_2SO_4$ of from 0.3 g/L to 15 g/(a solvent is water).

When the microorganisms related to the present embodiment are cultured, the culture condition is not particularly limited, and the culture is carried out while appropriately controlling pH and temperature. Aerobic condition or anaerobic condition may be used, but preferably aerobic condition may be used. Aeration rate is preferably from 0.2 L/min to 3 L/min per the culture medium of 1 L, and more preferably from 0.5 L/min to 2 L/min. Further, stirring speed is preferably from 200 rpm to 1000 rpm and more preferably from 500 rpm to 800 rpm. By doing as described above, there can be obtained a microbial cell to give a large amount of hydroxycarboxylic acid production per weight of the microbial cells. Further, the culture may be carried out by using a gas-bubble column or the like which can guarantee a supply of dissolved oxygen corresponding to the above conditions of the aeration rate and stirring speed.

Preferred is pH of from 5 to 8, more preferred is pH of from 7.0 to 7.4, most preferred is pH of 7.2. By doing this, there can be obtained a microbial cell to give a large amount of hydroxycarboxylic acid production per weight of the microbial cells.

Further, the temperature is preferably from 25° C. to 40° C., more preferably from 33° C. to 37° C., and most preferably 35° C. By doing this, there can be obtained a microbial cell to give a large amount of hydroxycarboxylic acid production per weight of the microbial cells.

The time required for the culture is from 12 hours to 50 hours. By doing this, there can be obtained a microbial cell to give a large amount of hydroxycarboxylic acid production per weight of the microbial cells.

As a solvent used in the production method according to the present invention, there may be exemplified buffer solutions such as potassium phosphate buffer solution, the aforementioned culture medium used for the culture of a microorganism, and pure water. Further, the reaction may be carried out by contacting microorganism microbial cells obtained from the previous culture to a mixture liquid of aliphatic polyhydric alcohol of the raw material and a solvent. For the microorganism microbial cells, there may be employed a method of using the culture broth itself after finishing the culturing or a method of using only the microbial cells recovered from the culture broth.

Upon the reaction in the production method of the present embodiment, the reaction condition is not particularly limited and the reaction is carried out while appropriately controlling pH and temperature.

For example, preferably pH is from 6 to 9, more preferably from 7.0 to 8.0, and most preferably 7.2. By doing this, there can be obtained an effect to enhance an amount of hydroxycarboxylic acid production per an amount of the microbial cells added to the reaction solution.

The temperature is preferably in a range of from 20° C. to 45° C., more preferably from 30° C. to 40° C., and most preferably 35° C. By doing this, there can be obtained an effect to enhance an amount of hydroxycarboxylic acid production per an amount of the microbial cells added to the reaction solution.

Furthermore, the reaction may be preferably carried out at aerobic condition. Aeration rate is preferably from 0.1 L/min to 2.0 L/min per 1 L of the reaction solution, and more preferably from 0.2 L/min to 1.0 L/min. In addition, stirring speed is preferably from 200 rpm to 1000 rpm and more preferably from 400 rpm to 800 rpm. By doing this, there can be obtained an effect to enhance an amount of hydroxycarboxylic acid production per an amount of the microbial cell added to the reaction solution. Further, the reaction may be carried out by using a gas-bubble column or the like which can guarantee a supply of dissolved oxygen corresponding to the aeration rate and stirring speed conditions described above.

Further, the reaction time is to be from 12 hours to 96 hours so that a hydroxycarboxylic acid can be obtained in the yield of 80% or more.

A process for recovering a hydroxycarboxylic acid accumulated in the obtained reaction solution as described above is not particularly limited. But, there can be adopted, for example, a process comprising removing the microbial cells from the reaction solution by centrifugation or the like and then using a synthetic adsorbent resin, a process using a precipitant, a process for separating a hydroxycarboxylic acid according to other usual collection and separation methods.

Production Example 1

Construction of *Escherichia coli* MG1655nadR-Deleted Strain

The entire base sequence of the genome DNA of *Escherichia coli* MG1655 strain has been already reported in GenBank accession number U00096, and the nadR gene is encoded at the bases of from Base No. 4625317 to Base No. 4626570 in the base sequence. Oligonucleotides represented by Sequence No. 1 (AGGAAGTGCCATTCTGATTGG) and Sequence No. 2 (GGAATTCGTATATCTCAT-TATAAGTCGTCG), and Sequence No. 3 (GGAATTCGT-GATGAAACTGCTCAAAGG) and Sequence No. 4 (TTG-GTACCTGATGACCTGAGCTTCTCG), constructed on the basis of the gene information of the domain near the nadR gene of the genome DNA of the *Escherichia coli* MG1655 strain, were used for a PCR amplification using the genome DNA of *Escherichia coli* MG1655 strain as a template. The obtained DNA fragment was digested with restriction enzymes NdeI and EcoRI, and EcoRI and KpnI, respectively, to obtain fragments of about 850 bp and 970 bp, respectively.

These DNA fragments were mixed with a fragment obtained by digestion of a temperature-sensitive cloning vector pTH18csI (GenBank accession number AB019610) (Hashimoto-Gotoh, T., Gene, 241, 185-191 (2000)) with NdeI and KpnI, ligated using a ligase, and then transformed with an *Escherichia coli* DH5α (produced by Toyobo Co., Ltd.), to obtain a transformant which grows on an LB agar plate at 30° C. containing 10 μg/mL of chloramphenicol. The obtained colony was cultured in an LB liquid culture medium containing 10 μg/mL of chloramphenicol at 30° C. overnight, and a plasmid was recovered from the obtained microbial cells. This plasmid was digested with EcoRI, and ligated using a ligase with a kanamycin resistant gene obtained by digestion of pUC4K plasmid (GenBank accession number X06404) (Pharmacia) with EcoRI.

The thus-obtained plasmid was transformed at 30° C. with an *Escherichia coli* MG1655 strain, cultured in an LB liquid culture medium containing 10 μg/mL of chloramphenicol and 50 μg/mL of kanamycin at 30° C. overnight, to obtain a transformant. The obtained transformant was inoculated in a culture medium containing 50 μg/mL of kanamycin and cultured at 30° C. overnight. Next, in order to obtain the cultured microbial cells thereof, the cultured transformant was applied on an LB agar plate containing 50 μg/mL of kanamycin to obtain colonies growing at 42° C. The obtained colonies were cultured in an LB liquid culture medium containing 50 μg/mL of kanamycin at 30° C. overnight, and again applied on an LB agar plate containing 50 μg/mL of kanamycin to obtain colonies growing at 42° C.

From the grown colonies, 100 colonies were picked up randomly, and each of them was grown on an LB agar plate containing 50 μg/mL of kanamycin and an LB agar plate containing 10 μg/mL of chloramphenicol, to select chloramphenicol-sensitive clones growing only on the LB agar plate containing kanamycin. Furthermore, in a wild strain MG1655, a fragment of about 3.3 kbp at the domain near the nadR gene containing the nadR gene was amplified by PCR using the chromosome DNA of these desired clones, the amplified fragments were treated with a restriction enzyme HindIII which has no recognition sequence to the nadR gene and has a recognition sequence to a kanamycin-resistant gene, to select a strain in which the nadR gene was substituted by the kanamycin-resistant gene, and the obtained strain was named as a MG1655nadR gene-deleted strain (hereinafter may be simply referred to as ΔnadR strain).

Also, the *Escherichia coli* MG1655 can be obtained from American Type Culture Collection.

Production Example 2

Construction of *Escherichia coli* MG1655glcDEF-Deleted Strain

The entire base sequence of the genome DNA of *Escherichia coli* has been already reported (GenBank accession number U00096), and the base sequence of a gene (may be referred to as glcDEF herein below) of glycolate oxidase of *Escherichia coli* has been also already reported (GenBank accession number L43490).

Oligonucleotides of Sequence No. 5 (TTGGTACCGT-TCTGCCAGCAACTGACG) and Sequence No. 6 (TGTCTAGAGTACCTCTGTGCGTCACTGG), and Sequence No. 7 (GCTCTAGACGCTTTGTTGTGTTGT-GTGG) and Sequence No. 8 (AACTGCAGGATCGGT-CAATGATTGCAGC), constructed on the basis of the gene information of the domain near glcDEF of the genome DNA of the *Escherichia coli* MG1655 strain, were used for a PCR amplification. Each of the obtained DNA fragments was digested with restriction enzymes KpnI and XbaI, and XbaI and PstI, respectively, to obtain fragments of about 670 bp and 790 bp, respectively.

These DNA fragments were mixed with the fragment obtained by digestion of a temperature-sensitive cloning vector pTH18csI (GenBank accession number AB019610) (Hashimoto-Gotoh, T., Gene, 241, 185-191 (2000)) with KpnI and PstI, ligated using a ligase, and then transformed with the DH5α strain 30° C., to obtain a transformant growing on an LB agar plate containing 10 μg/mL of chloramphenicol.

The obtained colony was cultured in an LB liquid culture medium containing 10 μg/mL of chloramphenicol at 30° C. overnight, and a plasmid was recovered from the obtained microbial cells. The obtained plasmid was digested with XbaI, and subjected to a blunt-end treatment using T4 DNA polymerase. Using transposon Tn10 (GenBank accession number 301830) as a template, oligonucleotides of Sequence No. 9 (CAGCTGACTCGACATCTTGGTTACCG) and Sequence No. 10 (CAGCTGCAAGAGGGTCAT-TATATTTCG) were used for a PCR amplification to obtain a tetracycline-resistant gene, and this DNA fragment was treated with T4 DNA polynucleotide kinase to be ligated with the above plasmid subjected to the blunt-end treatment.

The obtained plasmid was transformed with an *Escherichia coli* MG1655 strain at 30° C. and cultured on an LB agar plate containing chloramphenicol 10 μg/mL and tetracycline 30 μg/mL at 30° C. overnight, to obtain a transformant. The obtained transformant was inoculated in a LB liquid culture medium containing 30 μg/mL of tetracycline and cultured at 30° C. overnight. Next, in order to obtain the cultured microbial cells thereof, the cultured transformant was applied on an LB agar plate containing 30 μg/mL of tetracycline to obtain colonies growing at 42° C. The obtained colonies were cultured in an LB liquid culture medium containing 30 μg/mL of tetracycline at 30° C. overnight, and again applied on an LB agar plate containing 30 μg/mL of tetracycline to obtain colonies growing at 42° C.

From the grown colonies, 100 colonies were picked up randomly, and each of them was grown on an LB agar plate containing tetracycline 30 μg/mL and an LB agar plate containing 10 μg/mL of chloramphenicol, to select chloramphenicol-sensitive clones growing only on the LB agar plate containing tetracycline. Furthermore, the domain near the glcDEF containing glcDEF was amplified by PCR using the chromosome DNA of these desired clones.

By this PCR, a fragment of about 4.0 kbp was amplified in the strain including a MG1655 wild strain in which glcDEF was not substituted by a tetracycline-resistant gene, while a fragment of about 2.2 kbp was amplified in the strain in which the glcDEF domain was substituted by a tetracycline-resistant gene. The stains in which a fragment of about 2.2 kbp was amplified were selected and named as MG1655glcDEF-deleted strain (hereinafter, may be referred to as ΔglcDEF strain).

Production Example 3

Construction of *Escherichia coli* MG1655nadR&glcDEF-Deleted Strain

For the ΔnadR strain obtained in Production Example 1, glcDEF was deleted in the same manner as in Production Example 2. The obtained strain was named as MG1655nadR&glcDEF-deleted strain (hereinafter, may be abbreviated as ΔnadRΔglcDEF strain).

Production Example 4

Construction of Lactaldehyde Reductase and Lactaldehyde Dehydrogenase Double-Expression Vector The base sequence of a gene (hereinafter, may be abbreviated as fucO) of lactaldehyde reductase of *Escherichia coli* has been already reported (GenBank accession number M31059). The base sequence of a gene (hereinafter, may be abbreviated as aldA) of lactaldehyde dehydrogenase of *Escherichia coli* has been also already reported (GenBank accession number M64541).

In order to acquire fucO, oligonucleotides represented by Sequence No. 11 (GCTCTAGACGGAGAAAGTCTTAT-GATGGCTAACAGAATGATTCTG) and Sequence No. 12 (GTGAAGCTTGCATTTACCAGGCGGTATGG) were used for a PCR amplification using the genome DNA of *Escherichia coli* MG1655 strain as a template, and the obtained DNA fragment was digested with restriction enzymes XbaI and HindIII to give a fucO fragment of about 1.2 kbp.

In order to acquire aldA, oligonucleotides represented by Sequence No. 13 (CGAATTCCGGAGAAAGTCTTATGT-CAGTACCCGTTCAACATCC) and Sequence No. 14 (GCTCTAGACTCTTTCACTCATTAAGACTG) were used for a PCR amplification using the genome DNA of *Escherichia coli* MG1655 strain as a template, and the obtained DNA fragment was digested with restriction enzymes EcoRI and XbaI to give a aldA fragment of about 1.5 kbp.

Furthermore, in order to acquire a glyceraldehyde 3-phosphate dehydrogenase (GAPDH) promoter, oligonucleotides represented by Sequence No. 15 (AACGAATTCTCGCAAT-GATTGACACGATTC) and Sequence No. 16 (ACAGAAT-TCGCTATTTGTTAGTGAATAAAAGG) were used for a PCR amplification using the genome DNA of *Escherichia coli* MG1655 strain as a template, and the obtained DNA fragment was digested with a restriction enzyme EcoRI to give a DNA fragment of about 100 bp which encodes a GAPDH promoter.

The above-mentioned three DNA fragments were mixed with the fragment obtained by digestion of plasmid pUC18 (produced by Toyobo Co., Ltd.) with restriction enzymes EcoRI and HindIII, ligated using a ligase, and then transformed with an *Escherichia coli* DH5α strain, to obtain a transformant growing on an LB agar plate containing 50 μg/mL of ampicillin. The obtained colony was cultured in an LB liquid culture medium containing 50 μg/mL of ampicillin at 37° C. overnight. The obtained plasmid was recovered from the obtained microbial cells and this plasmid was named as pGAPfucO-aldA.

Example 1

Construction of a ΔnadRΔglcDEF Strain Transformant by Lactaldehyde Reductase and Lactaldehyde Dehydrogenase Double-Expression Vector The plasmid pGAPfucO-aldA obtained in Production Example 4 was transformed with the ΔnadRΔglcDEF strain obtained in Production Example 3, and cultured on an LB agar plate containing 50 μg/mL of ampicillin at 37° C. overnight, to obtain ΔnadRΔglcDEF/pGAPfucO-aldA strain.

Production Example 5

Construction of a ΔglcDEF Strain Transformant by Lactaldehyde Reductase and Lactaldehyde Dehydrogenase Double-Expression Vector The plasmid pGAPfucO-aldA obtained in Production Example 4 was transformed with the ΔglcDEF strain obtained in Production Example 2, and cultured in an LB agar plate containing 50 μg/mL of ampicillin at 37° C. overnight, to obtain ΔglcDEF/pGAPfucO-aldA strain.

Example 2

Production of Glycolic Acid by ΔnadRΔglcDEF/pGAPfucO-aldA Strain

The ΔnadRΔglcDEF/pGAPfucO-aldA strain obtained in Example 1 was inoculated into 25 mL of LB Broth, Miller's culture broth (Difco244620) as a culture medium contained in a conical flask, and cultured overnight with stirring in 120 rpm at a culture temperature of 35° C., as preculture. Then, the whole amount of the preculture broth was transferred to a 1 L-fermentor (BMJ-01, culture apparatus manufactured by ABLE Corporation) containing 475 g of the culture medium of the composition shown below to carry out culture. The culture was carried out under the conditions of atmospheric pressure, an aeration rate of 0.5 L/min, a stirring speed of 800 rpm, a culture temperature of 35° C. and pH7.2 (adjusted with an aqueous $NH_3$ solution). After the initial glucose was completely exhausted under the above conditions under the above conditions, glucose of the total amount of 40 g was supplied at a variable rate to make about less than 0.1 g/L of glucose concentration in the culture medium for the remaining time.

<The Culture Medium Composition>
Polypeptone: 7 g/L
Glucose: 30 g/L
$Fe_2SO_4$: 0.09 g/L
$K_2HPO_4$: 2 g/L
$KH_2PO_4$: 2 g/L
$MgSO_4.7H_2O$: 2 g/L
$(NH_4)_2SO_4$: 5 g/L
Solvent: water The microbial cell at 24 hours after starting the culturing was collected by centrifugation (8,000 rpm for 20 minutes). The wet microbial cells of 4.5 g after collecting the microbial cells was weighed and then suspended in distilled water together with ethylene glycol of 65 g to obtain 500 mL of the final liquid amount. The suspension was transferred to a fermentor of a culture apparatus BMJ-01 manufactured by ABLE Corporation to carry out the reaction for 70 hours. The reaction was carried out under the conditions including atmospheric pressure, an aeration rate of 0.25 L/min, a stirring speed of 550 rpm, a culture temperature of 35° C. and pH7.2 (adjusted with an aqueous $NH_3$ solution). The amount of glycolic acid accumulated in the obtained reaction solution was quantified by using high speed liquid chromatography produced by Hitachi, Ltd. at the conditions described below.

Column: ULTRON PS-80 H (produced by Shinwa Chemical Industries Ltd.)
Eluted solution: perchloric acid aqueous solution (pH2.1)
Flow rate: 1.0 mL/min
Detector: UV detector
Wavelength for measurement: 280 nm Further, the dry microbial cell weight of the microbial cells used in the reaction was obtained from the dry weight after drying a part of wet microbial cells at 50° C.

The amount of produced glycolic acid was 27.1 g per 1 g of the dry microbial cell of the ΔnadRΔglcDEF/pGAPfucO-aldA strain.

Here, the growth rate of the ΔnadRΔglcDEF/pGAPfucO-aldA strain was the same as that of the ΔglcDEF/pGAPfucO-aldA strain in Comparative Example 1, and it was confirmed that the growth delay by disruption of the nadR gene did not occur.

Comparative Example 1

Production of Glycolic Acid by ΔglcDEF/pGAPfucO-aldA Strain

For the ΔglcDEF/pGAPfucO-aldA strain obtained in Production Example 5, the culture and the production of glycolic acid were carried out in the same manner as in Example 2. The amount of produced glycolic acid was 20.2 g per 1 g of the dry microbial cell of the ΔglcDEF/pGAPfucO-ald strain.

Reference Example 1

Measurement of Intracellular Content of Nicotinamide Adenine Dinucleotide in ΔnadRΔglcDEF/pGAPfucO-aldA Strain and ΔglcDEF/pGAPfucO-aldA Strain The ΔnadRΔglcDEF/pGAPfucO-aldA strain and ΔglcDEF/pGAPfucO-aldA strain were cultured in the same manner as in Example 2.

Each of the ΔnadRΔglcDEF/pGAPfucO-aldA strain and ΔglcDEF/pGAPfucO-aldA strain at 24 hours after starting the culture were respectively collected in an amount of 1 mL into two microcentrifuge tubes and centrifuged at 4° C. to collect the microbial cells. Using one of the two microcentrifuge tubes for measuring NAD and the other for measuring NADH, the treatment described below was respectively carried out.

The sample for measuring NAD was suspended by adding 400 µL of 0.04 mol/L hydrochloric acid aqueous solution per 1.5 mg of the collected wet microbial cells. The suspension was heated at 90° C. for 3 minutes, and then rapidly cooled in an ice bath. Using the supernatant of this treated liquid, the reaction solution of the composition as described below was prepared. Further, 1 mol/L Tris-HCl of pH9.0 was used. Also, as an alcohol dehydrogenase, alcohol dehydrogenase (A3263, produced by Sigma Chemical Co.) was used by dissolving it with 10 mmol/L of Tris-HCl (pH8.8) to make 400 units/mL (provided that 1 unit is a minimum amount required for transforming ethanol of 1 µmol to acetaldehyde under the conditions of pH8.8 and 25° C. for 1 minute). Absorption at 450 nm of the reaction solution was measured according to the protocol of Tetra Color ONE (produced by SEIKAGAKU CORPORATION). Further, a NAD solution produced by Sigma Chemical Company was subjected to the same treatment and measurement to obtain a calibration curve, and the NAD concentration in the sample was obtained.

The sample for measuring NADH was suspended by adding 400 µL of 0.04 mol/L potassium hydroxide aqueous solution per 1.5 mg of the collected wet microbial cells. The suspension was heated at 90° C. for 3 minutes, and then rapidly cooled in an ice bath. Using the supernatant of this treated liquid, the reaction solution of the composition described below was prepared. Further, 1 mol/L Tris-HCl of pH8.8 was used. Also, as an alcohol dehydrogenase, alcohol dehydrogenase (A3263, produced by Sigma Chemical Co.) was used by dissolving it with 10 mmol/L of Tris-HCl (pH8.8) to make 400 units/mL (provided that 1 unit is a minimum amount required for transforming ethanol of 1 µmol to acetaldehyde under the conditions of pH 8.8 and 25° C. for 1 minute).

Absorption at 450 nm of the reaction solution was measured according to the protocol of Tetra Color ONE (produced by SEIKAGAKU CORPORATION). Further, a NADH solution produced by Sigma Chemical Company was subjected to the same treatment and measurement to obtain a calibration curve, and the NADH concentration in the sample was obtained.

From the results, the NAD content and NADH content of the ΔnadRΔglcDEF/pGAPfucO-aldA strain were increased by 1.7 times and 1.6 times, respectively, compared to the ΔglcDEF/pGAPfucO-aldA strain. From this, it was confirmed that the ability to produce NAD and NADH, that is, nicotinamide adenine dinucleotide was enhanced in the ΔnadRΔglcDEF/pGAPfucO-aldA strain in which the nadR gene was deleted.

<Composition of the Reaction Solution>
Sample supernatant: 25 μL
1 mol/L Tris-HCl: 25 μL
25% ethanol: 10 μL
Pure water: 20 μL
Tetra Color ONE (produced by SEIKAGAKU CORPORATION): 10 μL
Alcohol dehydrogenase: 10 μL Production Example 6

Construction of Lactaldehyde Reductase, Lactaldehyde Dehydrogenase and NADH Dehydrogenase Triple-Expression Vector The base sequence of a gene (hereinafter, may be abbreviated as ndh) of NADH dehydrogenase of *Escherichia coli* has been already reported (GenBank accession number V00306).

In order to acquire ndh, oligonucleotides represented by Sequence No. 17 (CGAATTCCGGAGAAAGTCTTATGACTACGGCATTGAAAAAGATTGTG) and Sequence No. 18 (GGTCTAGACGATTAATGCAACTTCAAACG) were used for a PCR amplification using the genome DNA of *Escherichia coli* MG1655 strain as a template, to obtain a ndh fragment of about 1.3 kbp. The obtained ndh fragment was treated with T4 DNA polynucleotide kinase. This DNA fragment was mixed with a fragment obtained by that the pGAPfucO-aldA plasmid constructed in Production Example 4 was digested with HindIII and then subjected to a blunt-end treatment and a dephosphorylation treatment, ligated using a ligase, and transformed with *Escherichia coli* DH5α strain (produced by Toyobo Co. Ltd.), to obtain a transformant growing on an LB agar plate containing 50 μg/mL of ampicillin. The obtained colonies were cultured in an LB liquid culture medium containing 50 μg/mL of ampicillin at 37° C. overnight, and a plasmid was recovered from the obtained microbial cells, and the obtained plasmid was named as pGAPfucO-aldA-ndh.

Example 3

Construction of a ΔnadRΔglcDEF Strain Transformant by Lactaldehyde Reductase, Lactaldehyde Dehydrogenase and NADH Dehydrogenase Triple-Expression Vector The plasmid pGAPfucO-aldA-ndh obtained in Production Example 6 was transformed with the ΔnadRΔglcDEF obtained in Production Example 3, and cultured in an LB agar plate containing 50 μg/mL of ampicillin at 37° C. overnight, to obtain ΔnadRΔglcDEF/pGAPfucO-aldA-ndh strain.

Example 4

Production of Glycolic Acid by ΔnadRΔglcDEF/pGAPfucO-aldA Strain

For the ΔnadRΔglcDEF/pGAPfucO-aldA-ndh strain obtained in Example 3, the culture and the production of glycolic acid were carried out in the same manner as in Example 2. Further, compared to the result of the culture in Example 2, growth delay by enhancing the ndh for this strain was not observed. The amount of produced glycolic acid per 1 g of the dry microbial cells of the ΔnadRΔglcDEF/pGAPfucO-aldA-ndh strain is shown in Table 1 together with the results in Comparative Example 1 and Example 2.

From the comparison of Comparative Example 1 and Example 2, the ability to produce glycolic acid was enhanced by 1.3 times due to enhancing the ability to produce nicotinamide adenine dinucleotide.

Further, from the comparison of Comparative Example 1 and Example 4, the ability to produce glycolic acid was enhanced by 3.6 times due to enhancing the ability to produce nicotinamide adenine dinucleotide and due to enhancing the ability to regenerate oxidized form of nicotinamide adenine dinucleotide

TABLE 1

| | ΔglcDEF/ pGAPfucO-aldA strain (Comparative Example 1) | ΔnadRΔglcDEF/ pGAPfucO-aldA strain (Example 2) | ΔnadRΔglcDEF/ pGAPfucO-aldA-ndh strain (Example 4) |
|---|---|---|---|
| The amount of produced glycolic acid per 1 g of the dry microbial cells (g) | 20.2 | 27.1 | 72.5 |

Production Example 7

Construction of Lactaldehyde Reductase, Lactaldehyde Dehydrogenase and Nicotinic Acid Phosphoribosyltransferase Triple-Expression Vector The base sequence of a gene (hereinafter, may be abbreviated as pncB) of nicotinic acid phosphoribosyltransferase of *Escherichia coli* has been already reported (GenBank accession number J05568).

In order to acquire pncB, oligonucleotides represented by Sequence No. 19 (CGTGCAATTGCCGGAGAAAGTCTTATGACACAATTCGCTTCTC) and Sequence No. 20 (CGCTCTAGATTAACTGGCTTTTTTAATATGCG) were used for a PCR amplification using the genome DNA of *Escherichia coli* MG1655 strain as a template, to obtain a pncB fragment of about 1.2 kbp. Further, the obtained pncB fragment was treated with T4 DNA polynucleotide kinase. This DNA fragment was mixed with a fragment obtained by that the pGAPfucO-aldA plasmid constructed in Production Example 4 was digested with HindIII and then subjected to a blunt-end treatment and a dephosphorylation treatment, ligated using a ligase, and then transformed with *Escherichia coli* DH5α strain (produced by Toyobo Co., Ltd.), to obtain a transformant growing on an LB agar plate containing 50 μg/mL of ampicillin. The obtained colonies were cultured in an LB liquid culture medium containing 50 μg/mL of ampicillin at 37° C. overnight, and a plasmid was recovered from the obtained microbial cells, and the obtained plasmid was named as pGAPfucO-aldA-pncB.

Example 5

Construction of ΔglcDEF Transformant by Lactaldehyde Reductase, Lactaldehyde Dehydrogenase and Nicotinic Acid Phosphoribosyltransferase Triple-Expression Vector The plasmid pGAPfucO-aldA-pncB obtained in Production Example 7 was transformed with the ΔglcDEF obtained in Production Example 2, and cultured in an LB agar plate containing 50 μg/mL of ampicillin at 37° C. overnight, to obtain a ΔglcDEF/pGAPfucO-aldA-pncB strain.

Example 6

Production of Glycolic Acid by ΔglcDEF/pGAPfucO-aldA-pncB Strain

For the ΔglcDEF/pGAPfucO-aldA-pncB strain obtained in Example 5, the culture and the production of glycolic acid were carried out in the same manner as in Example 2. The amount of produced glycolic acid per 1 g of the dry microbial cells in the ΔglcDEF/pGAPfucO-aldA-pncB strain was 26.7 g. Compared to the amount (20.2 g) of produced glycolic acid per 1 g of the dry microbial cells in the ΔglcDEF/pGAPfucO-aldA strain in Comparative Example 1, the ability to produce glycolic acid was enhanced by 1.3 times.

Reference Example 2

Measurement of Intracellular Content of Nicotinamide Adenine Dinucleotide in ΔglcDEF/pGAPfucO-aldA-pncB Strain For the ΔglcDEF/pGAPfucO-aldA-pncB strain obtained in Example 5, and the ΔglcDEF/pGAPfucO-aldA strain as compared, the culture was carried out and the NAD content and the NADH content were measured in the same manner as in Reference Example 1. As a result, the NAD content and the NADH content in the ΔglcDEF/pGAPfucO-aldA-pncB strain were 2.6 times and 2.1 times of the ΔglcDEF/pGAPfucO-aldA strain, respectively. From this, it was confirmed that the ability to produce NAD and NADH, that is, nicotinamide adenine dinucleotide was enhanced in the ΔglcDEF/pGAPfucO-aldA-pncB strain in which the pncB was enhanced.

Reference Example 3

Measurement of Intracellular Contents of NAD and NADH in ΔnadRΔglcDEF/pGAPfucO-aldA-ndh Strain and ΔnadRΔglcDEF/pGAPfucO-aldA Strain For the ΔnadRΔglcDEF/pGAPfucO-aldA-ndh strain and the ΔnadRΔglcDEF/pGAPfucO-aldA strain, the culture and the production of glycolic were carried out in the same manner as in Example 2. Samplings were carried out at a certain interval for the ΔnadRΔglcDEF/pGAPfucO-aldA-ndh strain and the ΔnadRΔglcDEF/pGAPfucO-aldA strain during the production of glycolic acid, and the intracellular contents of NAD and NADH were measured in the same manner as in Reference Example 1. FIG. 1 shows the NADH/NAD ratio (the NADH content/the NAD content) at each time. In FIG. 1, the horizontal axis indicates the reaction time (hr) and the vertical axis indicates the NADH/NAD ratio (the NADH content/the NAD content).

It was observed that a value of the NADH/NAD ratio was always small and NAD was regenerated from NADH in the ΔnadRΔglcDEF/pGAPfucO-aldA-ndh strain.

Production Example 8

Construction of NADH Dehydrogenase Expression Vector

The base sequence of a gene (hereinafter, may be abbreviated as ndh) of NADH dehydrogenase of *Escherichia coli* has been already reported (GenBank accession number V00306). In order to acquire ndh, oligonucleotides represented by Sequence No. 17 and Sequence No. 21 (AAAATAAGCTTC-GATTAATGCAACTTCAAACG) were used for a PCR amplification using the genome DNA of *Escherichia coli* MG1655 strain as a template, and the obtained DNA fragment was digested with restriction enzymes EcoRI and HindIII, to obtain a ndh fragment of about 1.3 kbp.

The obtained DNA fragment was ligated using a ligase with a fragment obtained by digesting plasmid pUC18 (produced by Toyobo Co., Ltd.) with restriction enzymes EcoRI and HindIII, and then transformed with *Escherichia coli* DH5α strain (produced by Toyobo Co., Ltd.), to obtain a transformant growing on an LB agar plate containing 50 μg/mL of ampicillin. The obtained colonies were cultured in an LB liquid culture medium containing 50 μg/mL of ampicillin at 37° C. overnight. The plasmid was recovered from the obtained microbial cells to confirm whether the DNA fragment of ndh was correctly inserted, and then treated with restriction enzyme EcoRI and further subjected to dephosphorylation.

Further, in order to acquire a GAPDH promoter, oligonucleotides represented by Sequence No. 15 and Sequence No. 16 were used for a PCR amplification using the genome DNA of *Escherichia coli* MG1655 strain as a template, and the obtained DNA fragment was digested with restriction enzyme EcoRI, to obtain a DNA fragment of about 100 bp encoding a GAPDH promoter. This DNA fragment was ligated using a ligase with the plasmid subjected to the treatment with EcoRI and the dephosphorylation treatment as described above, and then transformed with *Escherichia coli* DH5α strain (produced by Toyobo Co., Ltd.), to obtain a transformant growing on an LB agar plate containing 50 μg/mL of ampicillin. The obtained colonies were cultured in an LB liquid culture medium containing 50 μg/mL of ampicillin at 37° C. overnight. The plasmid was recovered from the obtained microbial cells to confirm whether the fragment of the GAPDH promoter was correctly inserted, and this plasmid was named as pGAPndh.

Example 7

Construction of ΔnadR Strain Transformant by NADH Dehydrogenase Expression Vector The ΔnadR strain obtained in Production Example 1 and the ΔnadRΔglcDEF obtained in Production Example 3 were transformed with the plasmid pGAPndh obtained in Production Example 8, and cultured in an LB liquid culture medium containing 50 μg/mL of ampicillin at 37° C. overnight, to obtain a ΔnadR/pGAPndh strain and a ΔnadRΔglcDEF/pGAPndh strain.

Production Example 9

Construction of MG1655 Strain Transformant by NADH Dehydrogenase Expression Vector

*Escherichia coli* wild-type MG1655 strain was transformed with the plasmid pGAPndh obtained in Production Example 8, and cultured in an LB liquid culture medium containing 50 μg/mL of ampicillin at 37° C. overnight, to obtain a MG1655/pGAPndh strain.

Example 8

Production of Glycolic Acid by ΔnadR/pGAPndh Strain and ΔnadRΔglcDEF/pGAPndh Strain The ΔnadR/pGAPndh strain, the ΔnadRΔglcDEF/pGAPndh strain obtained in Example 7, and the ΔnadR strain, the MG1655/pGAPndh and the wild-type MG1655 strain as a control group were respectively inoculated into 5 mL of a culture medium contained in a test tube which was prepared by adding glucose to LB Broth, Miller's culture broth (Difco244620) so as to make 0.2% of the final concentration, and cultured overnight with stirring in 200 rpm at a culture temperature of 37° C. After the whole amount of the culture broth was centrifuged and a weight of the obtained wet microbial cells was measured, 1 mL of the reaction solution as described below was prepared and stirred using a test tube at 200 rpm at 30° C., to produce glycolic acid for 48 hours.

<Composition of the Reaction Solution>

1 mol/L Potassium phosphate buffer solution (pH8.0): 250 μL

Ethylene glycol: 50 μL

Microbial cells: total microbial cell recovered from the culture broth

Adjusted to 1 mL with pure water.

The amounts of produced glycolic acid per 1 g of the wet microbial cells of each strain are shown in Table 2. It was observed that the ability to produce glycolic acid was significantly enhanced in the ΔnadR/pGAPndh strain and the ΔnadRΔglcDEF/pGAPndh strain.

TABLE 2

| | MG1655 | MG1655/pGAPndh | ΔnadR | ΔnadR/pGAPndh | ΔnadRΔglcDEF/pGAPndh |
|---|---|---|---|---|---|
| The amounts of produced glycolic acid per 1 g of the wet microbial cells (g) | 0.16 | 0.16 | 0.18 | 0.24 | 0.25 |

Example 9

Figure 2:
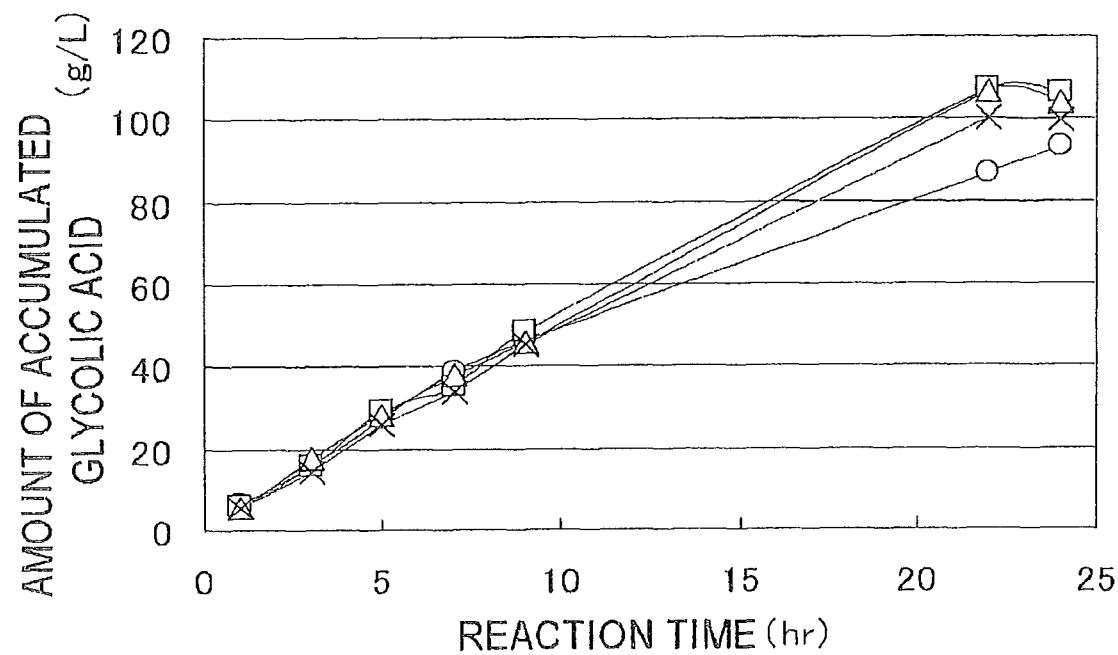
FIG. 2 It is a graph which shows the time-course change in an amount of accumulated glycolic acid in Example 9:
○ in the figure indicates the results from the reaction at 30° C.;
□ in the figure indicates the results from the reaction at 35° C.;
Δ in the figure indicates the results from the reaction at 37° C.;
X in the figure indicates the results from the reaction at 40° C.

Investigation on Temperature Condition of Reaction for Producing Glycolic Acid by ΔnadRΔglcDEF/pGAPfucO-aldA-ndh Strain For the ΔnadRΔglcDEF/pGAPfucO-aldA-ndh strain obtained in Example 3, the culture was carried out in the same manner as in Example 2. It was provided that the concentration of polypeptone in the culture medium was to be 1 g/L. For the obtained microbial cells, the reaction for producing glycolic acid was carried out in the same manner as in Example 2. It was provided that an amount of the wet microbial cells added to the reaction was 7 g, the stirring speed was 750 rpm, the reaction time was 24 hours, and the reaction temperature was 30° C., 35° C., 37° C., and 40° C., respectively. FIG. 2 shows the amount of accumulated glycolic acid in this case. In FIG. 2, the horizontal axis indicates the reaction time (hr) and the vertical axis indicates the amount (g/L) of accumulated glycolic acid.

It was observed that a sufficient amount of glycolic acid can be produced by the ΔnadRΔglcDEF/pGAPfucO-aldA-ndh strain even under the above conditions.

Example 10

Figure 3:
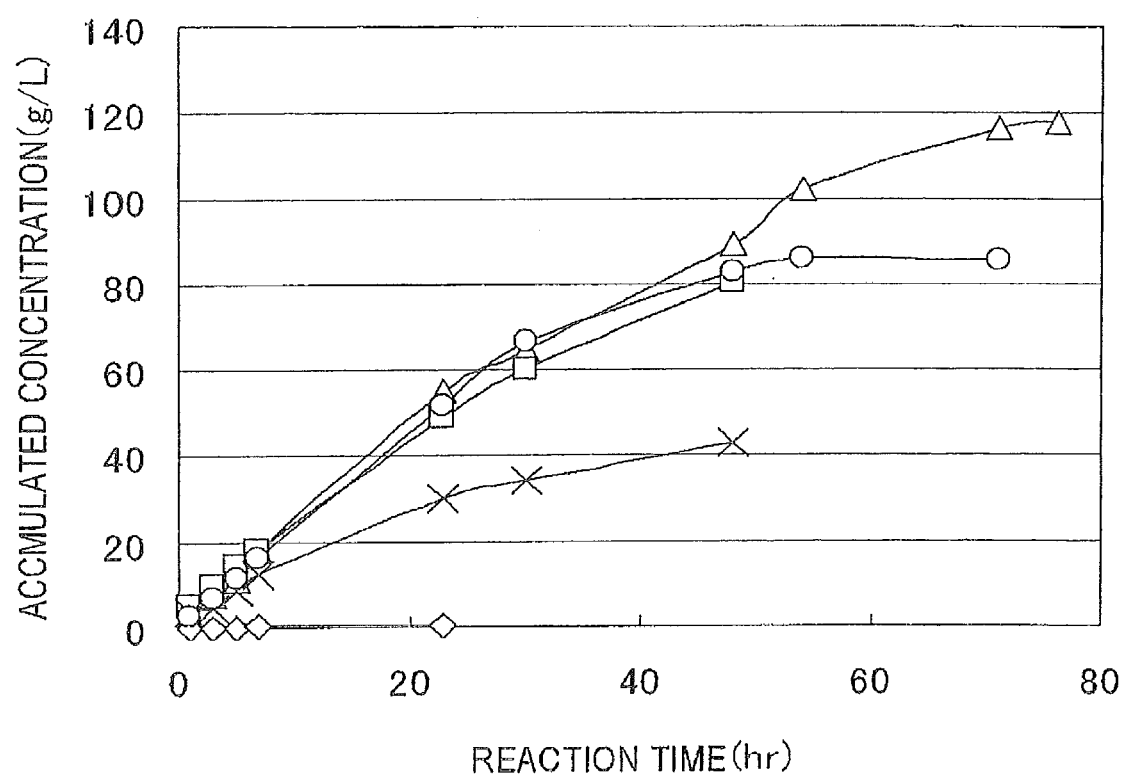
FIG. 3 It is a graph which shows the time-course change in an amount of accumulated glycolic acid in Example 10.

Investigation on pH Condition of Reaction for Producing Glycolic Acid by ΔnadRΔglcDEF/pGAPfucO-aldA-ndh Strain For the ΔnadRΔglcDEF/pGAPfucO-aldA-ndh strain obtained in Example 3, the culture was carried out in the same manner as in Example 2. It was provided that the concentration of polypeptone in the culture medium was to be 1 g/L. For the obtained microbial cells, the reaction for producing glycolic acid was carried out in the same manner as in Example 2. It was provided that pH of the reaction solutions was adjusted to pH7.7, pH7.2, pH6.5, pH6.0 and pH4.3, respectively to perform the reaction. FIG. 3 shows the amount of accumulated glycolic acid in this case. In FIG. 3, the horizontal axis indicates the reaction time (hr) and the vertical axis indicates the concentration (g/L) of accumulated glycolic acid.

It was observed that glycolic acid can be produced by the ΔnadRΔglcDEF/pGAPfucO-aldA-ndh strain at pH6.0 or higher.

INDUSTRIAL APPLICABILITY

The method for producing a hydroxycarboxylic acid or the microorganisms of the present invention can be used for producing hydroxycarboxylic acids such as glycolic acid and the like useful as a raw material for polymers or an intermediate for medicines.

The invention claimed is:

1. A method for producing glycolic acid from ethylene glycol using a microorganism, the method comprising using recombinant *Escherichia coli* which has an enhanced ability to produce nicotinamide adenine dinucleotide in *Escherichia coli* by deleting or substituting a nicotinamide adenine dinucleotide ("nadR") gene in the *Escherichia coli*, wherein the recombinant *Escherichia coli* has enhanced activity of at least one enzyme of lactaldehyde reductase and lactaldehyde dehydrogenase.

2. The production method as set forth in claim 1, wherein the recombinant *Escherichia coli* also has an enhanced ability to regenerate oxidized form of nicotinamide adenine dinucleotide by introducing into the *Escherichia coli* a plasmid comprising a gene of reduced-type nicotinamide adenine dinucleotide ("NADH") dehydrogenase derived from *Escherichia coli*.

3. The production method as set forth in claim 1 or claim 2, wherein the recombinant *Escherichia coli* has inactivated or lowered activity of glycolate oxidase as compared to the inherent activity of *Escherichia coli*.

* * * * *